(12) United States Patent
Statham et al.

(10) Patent No.: US 8,890,065 B2
(45) Date of Patent: Nov. 18, 2014

(54) APPARATUS AND METHOD FOR PERFORMING MICRODIFFRACTION ANALYSIS

(71) Applicant: Oxford Instruments Nanotechnology Tools Limited, Abingdon, Oxfordshire (GB)

(72) Inventors: Peter J. Statham, High Wycombe (GB); Angus Bewick, Abingdon (GB)

(73) Assignee: Oxford Instruments Nanotechnology Tools Limited, Oxon (GB)

( * ) Notice: Subject to any disclaimer, the term of this patent is extended or adjusted under 35 U.S.C. 154(b) by 0 days.

(21) Appl. No.: 14/350,306

(22) PCT Filed: Oct. 8, 2012

(86) PCT No.: PCT/GB2012/052489
§ 371 (c)(1),
(2), (4) Date: Apr. 7, 2014

(87) PCT Pub. No.: WO2013/050788
PCT Pub. Date: Apr. 11, 2013

(65) Prior Publication Data
US 2014/0252226 A1    Sep. 11, 2014

(30) Foreign Application Priority Data
Oct. 6, 2011  (GB) .................................. 1117256.6

(51) Int. Cl.
*H01J 37/26* (2006.01)
*H01J 37/29* (2006.01)
(52) U.S. Cl.
CPC ...................................... *H01J 37/29* (2013.01)
USPC ........ 250/305; 250/306; 250/307; 250/492.1; 250/492.3

(58) Field of Classification Search
CPC ..... H01J 37/26; H01J 37/295; H01J 2237/25; H01J 2237/2538; H01J 2237/2544; H01J 2237/255
USPC .............. 250/305, 306, 307, 310, 311, 492.1, 250/492.3
See application file for complete search history.

(56) References Cited

U.S. PATENT DOCUMENTS

2011/0058652 A1* 3/2011 Seidler ............................ 378/82

OTHER PUBLICATIONS

Ponchut C. et al., "Evaluation of Medipix-1 in X-ray Scattering and X-ray Diffraction Applications", Nuclerar Instruments & Methods in Physics Research. Section A: Accelerators, Spectrometers, Dectors, and Associated Equipment, Elsevier BV, North-Holland, Netherlands, vol. 510, No. 1-2, Sep. 1, 2003; pp. 29-34.

(Continued)

Primary Examiner — Nicole Ippolito
(74) Attorney, Agent, or Firm — Blank Rome LLP (57) ABSTRACT

An apparatus for detecting one or each of Kikuchi and Kossel diffraction patterns is provided. The apparatus comprises an electron column adapted in use to provide an electron beam (101) directed to wards a sample (102), the electron beam (101) having an energy in the range 2 keV to 50 keV, and a particle detector (111) for receiving and counting particles (103) from the sample (102) due to interaction of the electron beam (101) with the sample (102), the detector comprising an array of pixels (109) and having a count rate capability of at least 1000 particles per second for each pixel. The particle detector (111) is further adapted to provide electronic energy filtering of the received particles in order to count the received particles which are representative of the said diffraction pattern.

30 Claims, 4 Drawing Sheets

(56) References Cited

OTHER PUBLICATIONS

S. Dabritz et al., "Kossel and Pseudo Kossel CCD Pattern in Comparison with Electron Backscattering Diffraction Diagrams"; Applied Surface Science, vol. 179, No. 1-4; Jul. 1, 2001, pp. 38-44.

Deal et al., "Energy-filtered Electron Backscatter Diffraction", Ultramicroscopy, Elsevier, Amsterdam, NL, vol. 108, No. 2; Dec. 10, 2007, pp. 116-225.

Procz S. et al., "Energy Selective X-ray Imaging with Medipix", Nuclear Science Symposium Conference Record (NSS/MIC), 2010 IEEE, Oct. 30, 2010; pp. 3846-3851.

Faruqi, A.R., "Direct Electron Detectors for Electron Microscopy", Electron Emission Physics, Kevin L. Jensen, Elsevier, Acad. Press, vol. 145, Jan. 1, 2007; pp. 64-89.

Abhishek, Bhattacharyya et al., "Use of an Energy Filter to Improve the Spatial Resolution of Electron Backscatter Diffraction", Scanning, vol. 31, No. 3, May 1, 2009, pp. 114-121.

* cited by examiner

APPARATUS AND METHOD FOR PERFORMING MICRODIFFRACTION ANALYSIS

REFERENCE TO RELATED APPLICATIONS

The present application is a National Stage of PCT International Patent Application No. PCT/GB2012/052489, filed Oct. 8, 2012, which claims the benefit GB 1117256.6, filed Oct. 6, 2011, whose disclosures are hereby incorporated by reference in their entireties into the present disclosure.

FIELD OF INVENTION

The invention relates to an apparatus and method for performing microdiffraction analysis on a sample, in particular Kossel X-ray analysis and Electron Back Scatter Diffraction (EBSD) analysis in order to detect one or each of Kikuchi and Kossel diffraction patterns.

BACKGROUND

In microdiffraction analysis, an electron beam is directed towards a crystalline sample and the interaction of the electrons in the electron beam with the sample causes different types of particle to be produced. Two types of particle are of particular interest, these being backscattered electrons and X-rays. X-rays produced within the sample and diffracted by the lattice planes of the crystal are used in Kossel X-ray analysis, whereas electrons originating from the source electron beam elastically backscattered from the sample and having an energy close to the primary beam energy of the beam form the basis for Electron Back Scatter Diffraction analysis. These two analysis techniques can be used to measure properties of the sample, for example crystal orientation and strain.

In Kossel X-ray diffraction analysis, a focussed electron beam is directed towards a sample, typically in a scanning electron microscope (SEM). The interaction of the electron beam with the sample produces X-rays which are diffracted by the lattice planes of the sample. The "Kossel diffraction pattern" produced by the X-rays can be used to analyse the crystal orientation and other properties of the sample. The Kossel "signal" is a weak (low intensity), divergent beam of element-characteristic, diffracted X-rays emitted from the sample along with strong (high intensity) "background" beams of other particles, which are detected by conventional apparatus such as a photographic film or a solid-state electronic camera. Due to the "background" beams, the signal to background ratio is very small in SEM Kossel analysis, approximately 2%. The "background" beams have both undiffracted and diffracted components comprising different element-characteristic X-rays, X-rays forming a continuous energy spectrum, back-scattered electrons (with an approximately continuous energy spectrum), and UV to IR photons.

In order to improve the signal to background ratio in Kossel analysis a filter is typically placed between the sample and camera which absorbs the background beams while allowing the Kossel X-rays to pass through. The optimum filter composition and structure may be sample-dependent as the characteristic X-ray energy differs between samples. Example filters include a free-standing Al, Be, Fe or Ni film (or composite structures combining more than one of these elements); a film integrated as a window into the vacuum interface between the SEM vacuum chamber and camera; or a film deposited directly onto the camera.

The actual choice of filter used is a compromise between practicality, function and cost, and properties to consider include material, thickness, area and positioning in relation to the source and camera. The need for an absorption filter remains an inconvenient complication to the practical operation of the analysis.

A further complication with Kossel analysis is that the detected diffraction patterns are often complex, for example those from compound materials may be a superposition of patterns, wherein each different element of the compound contributes a different pattern dependent on the energy of its characteristic X-rays. Such superposed patterns are difficult to analyse. The conventional "pseudo" Kossel technique attempts to overcome this problem by inserting a single element foil between the electron source and the sample in order to provide a local source of monochromatic X-rays, rather than the X-ray source being within the sample itself. Alternatively, a coating may be used on the sample instead of a foil.

However, "pseudo" Kossel analysis has significant disadvantages, for example reduced spatial resolution and inconvenient complication to the practical operation of the apparatus. Further, where a coating is used instead of a foil, this can cause undesirable changes to the sample itself.

Electron Back Scatter Diffraction (EBSD) is a complementary technique to Kossel analysis. In EBSD, similarly to Kossel, a focussed electron beam is directed towards a sample, typically in a SEM. Here, the signal of interest is low-loss, back-scattered, diffracted electrons with energy close to the primary energy of the source electron beam, rather than the diffracted X-rays in Kossel analysis. These low-loss electrons are typically analysed in the form of a "Kikuchi diffraction pattern". However, as well as diffracted electrons from the sample, there are also background beams such as X-rays and low-energy electrons. Unlike with Kossel analysis, it is not possible to construct an absorption filter which will allow the transmission of the signal electrons whilst blocking the background X-rays and other background particles; and the conventional approach is to use no filter and accept that the signal to background ratio for EBSD is very low.

Hooghan et al, Microsc. Microanal. 10(Suppl 2), 2004, discloses a possible approach to increasing the signal to background ratio for EBSD by using an electrostatic element as a filter. This allows electrons to be filtered according to their energy, for example rejecting some lower-energy, background electrons. Even so, X-rays, being uncharged, are not filtered and so these still contribute to the background.

There are further disadvantages to such a filter. For example, the filter reduces the solid angle of detection, so reducing the angular range of the Electron Back Scatter Pattern (EBSP). There is also the requirement to operate with high voltages which complicates interfacing with an SEM; the filter is bulky, requiring more space inside the SEM chamber and the filter operates effectively only in a narrow, high-pass mode (imaging aberrations are large unless operated very close to the SEM's primary beam energy).

It is therefore desired to improve the filters used in both Kossel X-ray and EBSD analysis to increase the signal to background ratio and to facilitate simpler operation of the apparatus. Additionally, EBSD and Kossel analysis techniques are complementary and are beneficially both carried out on the same sample to measure crystal orientation, strain and other properties. However, this is currently a time-consuming and difficult process to carry out due primarily to the requirement of the absorption filter in Kossel analysis. If the EBSD analysis is desired to be carried out using an electrostatic filter then this further complicates the procedure. For example, if a sample is to be analysed in a SEM by both Kossel and EBSD techniques then the SEM may first be run with an ultra-thin Be filter in place in order to produce a Kossel diffraction pattern. For EBSD to subsequently be carried out on the same sample, the filter must first be removed, meaning downtime of the SEM. This removal (or insertion if EBSD is performed first) of the filter is particularly disadvantageous when a specific region of interest on the sample has been located for analysis and must be re-located between procedures. Additionally, "pseudo" Kossel analysis where the sample is coated is incompatible with EBSD analysis.

In U.S. Pat. No. 6,462,340, provision is made for a dual purpose device with moveable filter such that a single apparatus can be used for both the detection of EBSD and Kossel patterns. However, this still requires the movement of an absorption filter. Further filter properties such as its material and thickness may need to be changed depending on the particular application or sample.

SUMMARY OF INVENTION

In accordance with a first aspect of the present invention there is provided apparatus for detecting one or each of Kikuchi and Kossel diffraction patterns, the apparatus comprising: an electron column adapted in use to provide an electron beam directed towards a sample, the electron beam having an energy in the range 2 keV to 50 keV, and; a particle detector for receiving and counting particles from the sample due to interaction of the electron beam with the sample, the detector comprising an array of pixels and having a count rate capability to deal with at least 1000 particles per second for each pixel, and wherein; the particle detector is adapted to provide electronic energy filtering of the received particles in order to count the received particles which are representative of the said diffraction pattern.

In this context, a "particle detector" refers to a detector that converts the energy of each received particle into an electronic signal as opposed to an "indirect" detector that for example converts particle energy to light with a phosphor screen and uses intermediate optics to focus the light on to the sensor. The inefficiencies involved in optical elements for indirect detectors lead to a loss of detection sensitivity. Furthermore, indirect detectors typically generate a signal current that is representative of the energy x rate product for a stream of incident particles, whereas a particle detector can measure the signal from a individual particle.

The term "pixel" here refers generally to spatially separate sensitive regions of the detector, such that particles incident on two different pixels will be deemed to have hit two different regions of the detector. Therefore, "pixel" may refer to a conventional array of pixels in a direct electron detector or CCD as is known in the art, as well as independent regions of a silicon strip detector for example, where each "pixel" here is the region associated with each contact strip.

The apparatus of the first aspect of the invention advantageously removes the need for an absorption filter (in Kossel analysis) or bulky grid electrodes and high voltages (as in conventional EBSD) by applying electronic filtering after indiscriminately receiving particles from the sample. In other words, each received particle from the sample falling on the pixels of the detector produces an electronic signal proportional to its energy, and it is these electronic signals that are filtered. Two different particles with the same energy (for example a 10 keV X-ray photon and a 10 keV electron) will produce exactly the same output signal from the detector.

Therefore the apparatus of the present invention, in contrast to conventional Kossel apparatus, filters with respect to particle energy and not particle type.

Further, the output signal from the particle detector is a count per particle, and not the aggregated current due to the continuous arrival of particles as in conventional apparatus. Since the detector carries out electronic energy filtering of the indiscriminately received particles, a count is or is not obtained in accordance with the energy of each received particle.

A minimum detector count rate capability is necessitated by the data rate of EBSD and Kossel experiments. In some experiments, the data rate could easily reach 10000 events per second, and thus the detector of the present invention has a count rate capability, for each pixel, of 1000 events per second, preferably 10000 events per second and most preferably 100000 events per second. Such count rates are particularly important in this invention when each particle is indiscriminately received by the detector, and then filtered and counted, rather than particles being filtered before hitting the detector.

The received particles have a range of energies including energies representative of the said diffraction pattern and energies representative of a background. When an incident electron beam interacts with a sample, a range of particles with different energies are received by the detector, including elastically and inelastically scattered electrons, Kossel and background X-rays, and light. Kikuchi diffraction patterns are detected in EBSD analysis and are detected due to elastically scattered electrons with energy close to the primary beam energy of the electron source. Background particles in relation to Kikuchi diffraction patterns include low energy X-rays and inelastically scattered electrons having low energy.

On the other hand, the received particles representative of Kossel diffraction patterns are X-rays produced due to interaction of the electron beam with the sample which are then diffracted by the lattice planes. Background particles in this respect are high and low energy electrons.

The detector has at least one particle counter for counting the received particles which are representative of the said diffraction pattern. The at least one particle counter has a count rate of at least 1000 events per second, preferably 10000 events per second and most preferably 100000 events per second. In some implementations the array of pixels and the at least one particle counter are a unitary component with all of the features integrated onto one chip, these being generally termed a monolithic active pixel sensor (MAPS). However, in other implementations, the array of pixels is bump-bonded to the at least one particle counter and these are known as "hybrid" detectors or hybrid active pixel sensors (HAPS).

Each pixel comprises a semiconductor substrate for sensing particles. Examples of suitable semiconductors include silicon, GaAs, or Cd(Zn)Te. When a particle impinges on a pixel it deposits its energy in the semiconductor and creates an electron-hole pair, with the resulting charge forming an electronic signal. The electronic signal is then energy filtered by the detector in order to generate an output signal in accordance with the energy of each received particle.

Preferably, each pixel has a corresponding particle counter providing a "one to one" mapping between the pixels and the particle counters. In architectures where there are different numbers of pixels and particles counters, a "one to many" or "many to one" relationship is created. Ideally, the particle counters are arranged in an array corresponding to, and with the same pitch as, the array of pixels, although other arrangements are envisaged. In a HAPS detector the array of pixels is bump-bonded to the array of particle counters; however, both arrays could be a unitary member, such as in a MAPS.

Even more preferably, each particle counter produces an individual output signal in accordance with the energy of each received particle. Where each pixel has a corresponding particle counter, this advantageously increases the rate at which incident events can be counted. Data rates in EBSD and Kossel experiments could be as high as 10000 events per second per pixel or greater. Where each pixel has a corresponding particle counter, each particle counter has a count rate capability of at least 1000 events per second, preferably 10000 events per second. Higher count rate capabilities are also envisaged, such as 100000 events per second. Each pixel having a corresponding particle counter provides a distinct advantage in achieving suitably fast particle measurement over sequential readout detectors such as CCDs.

Importantly, detectors used in the current invention must be capable of particle counting at a fast enough rate.

Advantageously, the particle detector is adapted to provide electronic energy filtering with respect to at least one adjustable energy threshold. Electronic discrimination can be used to either reject or accept particles with energy greater or less than a threshold. For example, the particle detector can count all received particles having an energy greater than E1. Preferably the particle detector has an additional adjustable energy threshold so that it can count all particles that have energy greater than E1 and less than E2, where E2>E1. Preferably, received particles having an energy not satisfying the energy threshold conditions are not counted. This feature of the present invention is particularly beneficial as the electronic energy filtering is adapted to distinguish between received particles having an energy representative of the said diffraction pattern and received particles having an energy representative of a background.

As discussed above, the particles of interest with respect to Kikuchi diffraction patterns in EBSD analysis are high energy electrons, with background particles being low energy X-rays and electrons. The particle detector of the present invention can therefore be used to provide electronic energy filtering acting as a high-pass filter in order to count only those particles having energy greater than E1. Of course, there may be some "background" particles with an energy satisfying this threshold that will be counted, but this feature of the present invention provides a convenient way of increasing the signal to background ratio of the detected diffraction patterns without the requirement for bulky high voltage electrostatic filters.

Similarly, the detector may be set up to have two energy thresholds E1 and E2 acting as a band-pass filter, such that only received particles having an energy in the range [E1:E2] are counted. Kossel patterns are formed when X-rays of the same energy emitted from a point source are diffracted by the crystalline material of the sample. Thus, any particles with energies higher or lower than this energy introduce "background" into the pattern. When the sample contains more than one element there will be a different Kossel pattern corresponding to each characteristic element line. For example, in FIG. 4, it is clear that the X-ray spectrum of the alloy shows two strong characteristic emissions at 5.4 keV and 7.5 keV which give two different sets of Kossel lines corresponding to these two energies. Analysis of these patterns to establish the crystallography of the sample is more difficult when there are more than one set of lines. The band pass arrangement can be used to simplify the Kossel pattern and increase the signal to background ratio because electrons and other particles having an energy outside of this range and not representative of a particular Kossel diffraction pattern will not be counted and will therefore not contribute to the diffraction pattern. If only a single energy threshold is available, a "low-pass" energy filter is still advantageous as this will remove the background from higher energy electrons and confusing patterns from higher energy X-ray lines. This use of energy thresholding in respect of Kossel diffraction patterns removes the requirement for absorption filters used in conventional Kossel experiments.

Preferably, each individual particle counter is adapted to provide electronic energy filtering with respect to at least one adjustable energy threshold. In one example each particle counter is adapted to provide electronic energy filtering, with respect to at least one adjustable energy threshold, acting as a high-pass filter. In another example each particle counter is adapted to provide electronic energy filtering, with respect to at least one adjustable energy threshold, acting as a band-pass filter and in yet another example each particle counter is adapted to provide electronic energy filtering, with respect to at least one adjustable energy threshold, acting as a low-pass filter. As described above, a band-pass filter is desirable to increase the signal to background ratio in Kossel analysis. It is also possible to adjust the band-pass energy thresholds in order to obtain Kossel diffraction patterns for each different characteristic X-ray line emitted from compound samples. This is far more convenient than the implementation of foils in the "pseudo" Kossel method, and does not require any coating of the sample. As such, Kossel and EBSD analysis on a sample are fully compatible using the apparatus of the present invention.

Preferably, the apparatus further comprises a control device operable, in use, to adjust the at least one adjustable energy threshold between a first setting and a second setting. For example, at the first setting each of the particle counters may be adapted to provide electronic energy filtering acting as a band-pass filter and at the second setting each of the array of sensors may be adapted to provide electronic energy filtering acting as a high-pass filter. Advantageously, this means that the same apparatus can be used to perform both Kossel and EBSD analysis (and thus detect Kossel and/or Kikuchi diffraction patterns with the same detector) simply by switching the adjustable energy threshold between a first setting and a second setting respectively. There is no requirement for manipulation of a delicate filter as in conventional Kossel analysis or the electrostatic filters seen in EBSD. Further, the same area on a sample can be easily analysed by both EBSD and Kossel analysis simply by switching the setting of the energy threshold, rather than opening the SEM chamber and manipulating absorption filters or by the use of complicated vacuum feedthroughs.

Typically the apparatus also comprises an image processing unit adapted to generate image data from the detector. Preferably, the image processing unit is used to produce diffraction patterns for further analysis. The diffraction pattern is formed by measuring the intensity of the output signals at each pixel location. As the output signal corresponding to each pixel is a count, the intensity is simply the number of events in a certain energy range recorded at a pixel location.

Preferably, the electron column is a part of a scanning electron microscope (SEM) which provides beam energies in the range of 2 keV to 50 keV in normal operation. Typically, the arrangement will be such that the detector is on the same side of the sample as the electron source, such that the received particles have a component of their trajectory back along the electron beam axis with respect to the sample. However, the diffraction patterns can also be detected in transmission, where the detector is positioned on the opposite side of the sample to the electron beam. In this architecture the received particles do not have a component of their trajectory back along the electron beam axis, with respect to the sample. In transmission EBSD, the received "signal" consists of elastically scattered electrons that have travelled through the sample rather than having been reflected from it. Likewise, in transmission Kossel the received "signal" consists of X-rays that have travelled through the sample.

Preferably, the particle detector is a direct detector where the individual particles strike the detector directly and there is no requirement for intervening optics to focus an image on a sensor array. Such a detector will not be limited to the detection of electrons, and will also be capable of detecting other particles such as X-rays and photons with energy satisfying the threshold(s) of the detector. In principle, the surface of the direct detector could have a coating of scintillator material provided the scintillator decay time is fast enough to allow the signal from an individual particle to be measured without interference from residuals from previous particles. Additionally, different families of detector are envisaged, such as silicon strip detectors.

In accordance with a second aspect of the present invention there is provided a method for detecting one or each of Kossel and Kikuchi diffraction patterns, the method comprising: operating an electron column such that an electron beam having an energy in the range 2 keV to 50 keV impinges upon a sample; receiving, at a particle detector, particles from the sample due to interaction of the electron beam with the sample, the particle detector comprising an array of pixels, each pixel having a count rate capability to deal with at least 1000 particles per second; electronically filtering, at the particle detector, the energy of each received particle; and counting, at the particle detector and based on the electronic filtering, the received particles representative of the said diffraction pattern.

Preferably, the step of electronically filtering the energy of each received particle includes providing at least one adjustable energy threshold. This advantageously allows filtering of background beams in Kossel and EBSD analysis to be carried out electronically, removing the requirement for physical absorption or electrostatic filters, as described above.

Typically, the steps of electronically filtering and counting are carried out for each of the array of pixels. This advantageously allows for a high data count rate to cope with the data rate of EBSD and Kossel experiments.

Preferably, the method may further comprise the step of adjusting the adjustable energy threshold between a first setting and a second setting. This advantageously allows Kossel X-ray analysis and EBSD analysis to be performed on a sample, wherein when performing Kossel analysis the adjustable energy threshold is set to a first setting and when performing EBSD analysis the adjustable energy threshold is set to a second setting. Here, at the first setting the particle counters are adapted to provide electronic energy filtering acting as a band-pass filter and at the second setting the particle counters are adapted to provide electronic energy filtering acting as a high-pass filter. A particle counter according to the second aspect of the invention can also act as a low-pass filter.

This has the significant advantage of allowing two modes of microdiffraction analysis, namely detecting Kossel and/or Kikuchi diffraction patterns, to be implemented using the same apparatus by simply switching between the two modes via electronic filtering rather than the manipulation of physical absorption filters. This is particularly useful when carrying out both analysis techniques on a selected area of a sample. Conventionally, to analyse the selected area using both EBSD and Kossel, the absorption filter required for Kossel would have to be removed/inserted into the SEM chamber between analyses, causing experimental downtime and the possibility of equipment damage. It is also difficult to relocate the selected area for analysis after filter manipulation. However, using the present method, the selected area of the sample can be analysed by both Kossel and EBSD simply by switching the electronic thresholding between first and second settings.

Preferably, the particle detector provides two adjustable thresholds so that it can be operated as a band pass electronic filter. If only one threshold is available, an image can be acquired corresponding to a high pass filter at threshold, E1. Immediately after this image is acquired, a second image is acquired with the threshold set to a higher level, E2 without changing any other conditions. If the second image is subtracted from the first, the resultant image is effectively the same as the image formed by filtering with a band pass between E1 and E2. However, this subtraction of images will produce some additional noise compared to a true band pass electronic filter (i.e. one with two adjustable thresholds).

Using a band pass energy filter is particularly useful when performing Kossel X-ray analysis on a compound sample in order to differentiate between Kossel diffraction patterns produced by the X-ray emission lines from different elements in the sample. Simply adjusting a band pass filter to pick out a particular line energy is far more convenient and time-effective than performing conventional "pseudo" Kossel analysis with an auxiliary foil or coating.

DETAILED DESCRIPTION OF THE DRAWINGS

Figure 1:
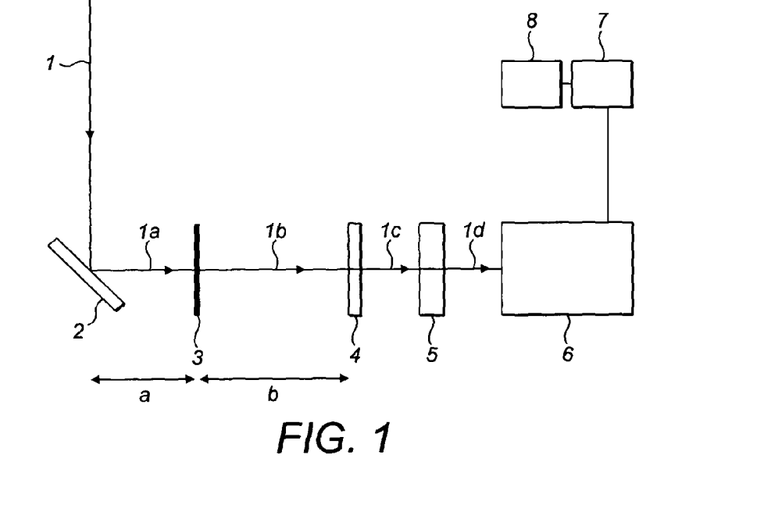
FIG. 1 shows a schematic arrangement of a conventional apparatus for performing microdiffraction analysis.

FIG. 1 shows a conventional apparatus used for performing Kossel X-ray analysis. A focussed electron beam 1 is directed towards a sample 2. Conventionally this is carried out in a scanning electron microscope (SEM), with the sample held on a platen in the SEM chamber at an angle tilted towards a filter 3 a distance a away from the sample 2. The electrons in the beam interact with the sample and produce X-rays which are diffracted by the crystal planes in the sample. This X-ray "signal" and background beams, collectively shown at 1*a*, impinge on filter 3. The background beams include Bremsstrahlung X-rays and backscattered electrons.

The filtered signal and background which together form beam 1*b* impinge on phosphor screen 4, a distance b from the filter 3, producing an optical signal and background beams collectively shown as beam 1*c*. Beam 1*c* passes through optical coupling 5, which could be a lens or fibre bundle, and produces optical signal and background beams, collectively shown at 1*d*, and the apparatus further comprises a CCD detector 6, image processing unit 7 and display unit 8. This apparatus can be used to display X-ray diffraction patterns generated by image processing unit 7 which can then be analysed to determine properties of the sample such as crystal lattice dimension and orientation.

In the conventional apparatus of FIG. 1, the phosphor screen 4 is sensitive to both X-rays and electrons (as well as to light). The signal is proportional to all of the charge generated in the phosphor screen by the signal and background beams. It is for this reason that the filter 3 is required (as discussed hereinabove) in order to absorb the background electrons and allow transmission of the signal X-rays towards the phosphor screen.

The use of a phosphor screen means that there is a conversion of the X-ray signal to an optical signal which is then imaged via the optical coupling 5, CCD detector 6 and image processing unit 7, and displayed on display unit 8. The optical conversion and coupling steps are inefficient and lead to a loss of detection sensitivity.

In EBSD analysis the conventional set up is substantially the same, however without the absorption filter 3. An electron beam is caused to impinge on a sample 2, typically in the chamber of an SEM, and the signal of interest, in this case elastically backscattered electrons, impinges upon the phosphor screen 4. This produces an optical signal which is imaged in the same manner as above, via the optical coupling 5, CCD detector 6 and image processing unit 7, before being displayed on display unit 8. In EBSD this image is the electron back scatter diffraction pattern (EBSP) which can be analysed to determine properties of the sample such as grain orientation and texture.

EBSD analysis may employ the use of an electrostatic filter as described in Hooghan et al, Microsc. Microanal. 10(Suppl 2), 2004, however this is bulky, taking up room in the SEM chamber, requires the use of high voltages which introduce practical issues of breakdown and safety and requires precise adjustment to avoid image distortion Referring now to FIG. 2, this shows a schematic arrangement of an apparatus for performing microdiffraction analysis on a sample according to an embodiment of the invention.

Figure 2:
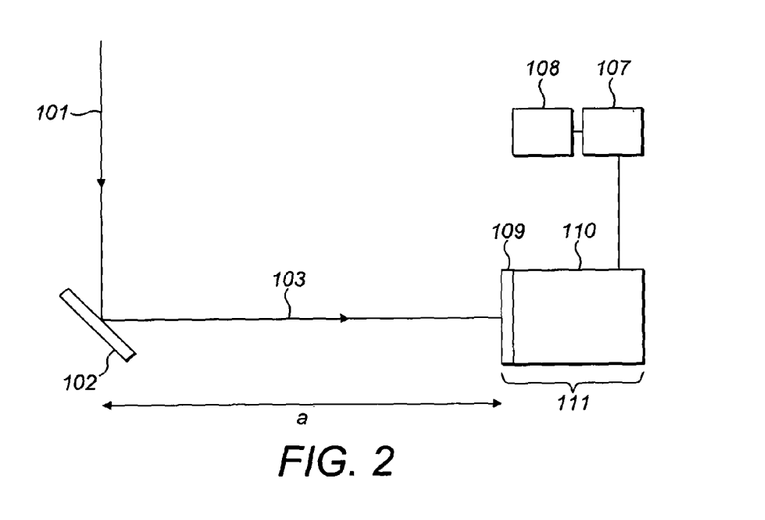
FIG. 2 shows a schematic arrangement of an apparatus for performing microdiffraction analysis according to an embodiment of the invention.

An electron beam 101 is directed towards and impinges upon a sample 102. The sample 102 is supported on a platen (not shown) in the chamber of a scanning electron microscope (SEM). The sample is tilted to a desired angle such that particles 103 (including elastically and inelastically backscattered electrons and X-rays) resulting from interaction of the electron beam with the sample are received by the detector 111. The particles received by the detector include both "signal" particles representative of a diffraction pattern—elastically scattered electrons in the case of EBSD and diffracted X-rays in the case of Kossel—as well as "background" particles such as low energy inelastically scattered electrons and Bremsstrahlung X-rays generated due to source electrons decelerating in the sample.

In the arrangement shown in FIG. 2, the detector is positioned on the same side of the sample as the incident electron beam; hence the arrangement is such that the particles received from the sample 103 have a component of their trajectory back along the beam direction 101 with respect to the sample 102. However, the arrangement it not limited to this "reflection" method, and it is also possible to position the detector 111 on the opposite side of the sample to the incident electron beam. In such a "transmission" arrangement, the particles received from the sample 103 do not have a component of their trajectory back along the beam direction 101 with respect to the sample 102.

The beam 103 from the sample is divergent, thus it is advantageous to position the detector 111 as close as possible to the sample so as to maximise the solid angle of particles impinging upon it. Typically, the distance "a" in FIG. 2 is approximately 15-20 mm.

Figure 3:
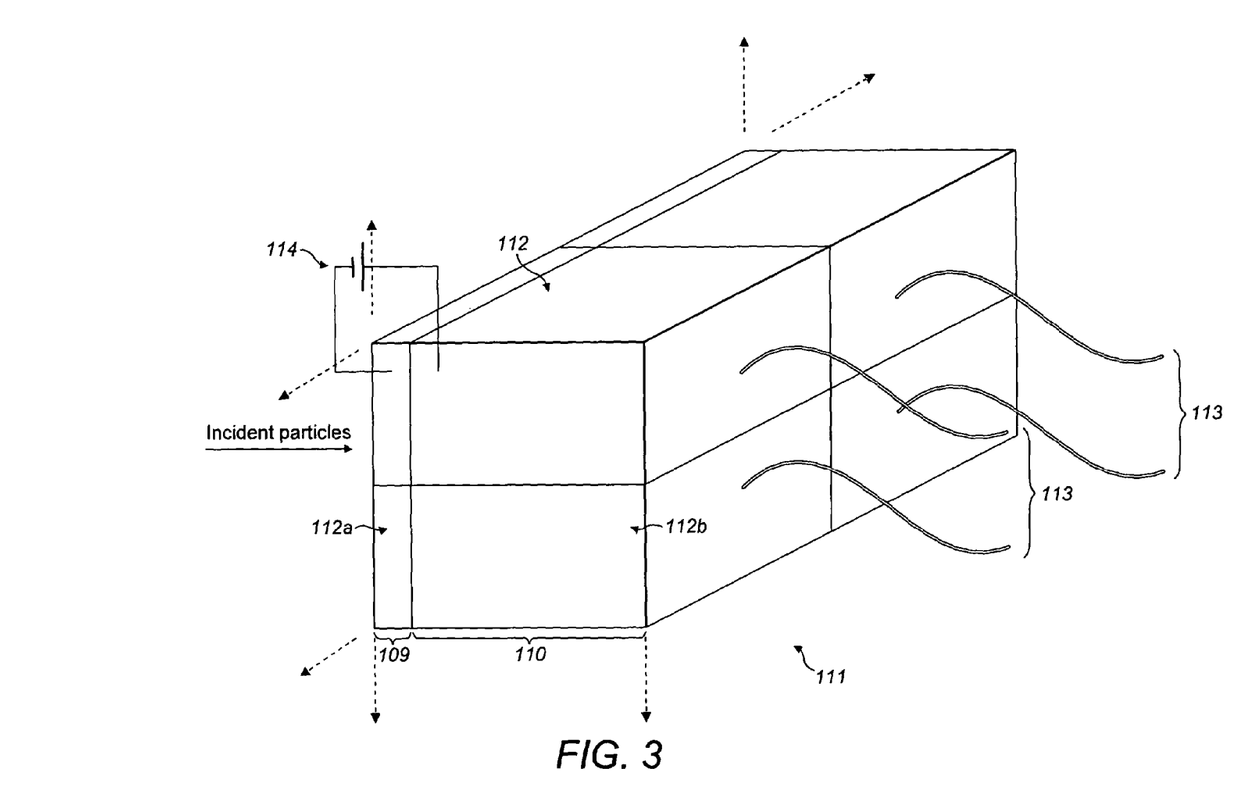
FIG. 3 is a schematic diagram of part of a detector according to an embodiment of the invention.

FIG. 3 is a diagram showing a section of detector 111 in one embodiment of the invention. The particle detector 111 is an example of a "direct detector", which does not require the phosphor screen 4 or the optic coupling 5 of the conventional apparatus. The detector comprises an array of pixels 112a. Four such pixels 112a are shown in FIG. 3; however a practical detector might typically comprise an array of 256×256 pixels, each of pitch 55 μm. The array of pixels (shown generally at 109) is typically a monolithic semiconductor such as silicon, GaAs, or Cd(Zn)Te, arranged into an array. In this embodiment the array of pixels is bump bonded to an array 110 of particle counters 112b, wherein the array of particle counters has the same pitch and arrangement as the pixel array 109. An individual particle counter is shown at 112b. In the embodiment shown in FIG. 3, each particle counter 112b has a corresponding pixel 112a providing a one to one mapping between the pixels and the particle counters, although one to many and many to one relationships are also envisaged. For example, the detector may have one particle counter 112b for every four pixels 112a.

As described above, in this embodiment the array of pixels is bump bonded to an array of particle counters. Such an arrangement is known as a "hybrid" detector or hybrid active pixel sensor (HAPS). However, it is also possible to use a detector where the array of pixels and the array of particle counters are one unitary member formed on a single chip. This type of arrangement is commonly called a monolithic active pixel sensor (MAPS).

Each particle counter 112b has its own electronic processing built in and generates its own output signal. Each particle counter 112b generates its own output signal along coupling 113 to image processing unit 107. In one embodiment the detector may correlate the output signals from each sensor to provide a single signal to the image processing unit 107 (see FIG. 2).

In one embodiment the pixel array 109 further comprises metal electrodes (not shown) arranged in a square lattice which are used to apply a bias voltage 114 across the layer (illustrated schematically in FIG. 3). Thus, when an incident particle (such as an electron or X-ray photon) is incident on a pixel 112a, the energy of that particle is deposited in the pixel 112a and an electron-hole pair is formed in the semiconductor. Under the influence of the applied electric field, the charge due to the created electrons and holes drifts to a collecting electrode (not shown) and is transferred across the bump bond to the corresponding particle counter 112b. The amount of charge collected is proportional to the number of electron-hole pairs produced, which in turn is proportional to the energy deposited in the pixel 112a. Therefore the electrical signal from the pixel 112a is in accordance with the energy of the received particle.

Each particle counter 112b has pulse processing electronics, wherein each "event" to be counted is a pulse of charge created by an incident particle depositing energy in a pixel 112a. The pulse-processing electronics include an amplifier, a discriminator and a counter. One of the most important aspects of this invention is the count rate of the detector. The rate of incident particles hitting a detector in a Kossel or EBSD experiment could be 10,000 events per second. Therefore, in order to discriminate between particles of different energies, the particle counters of the detector must each be capable of counting at a count rate of 1000 events per second. Preferably, the particle counters can count at a rate of 10000 events per second and more preferably at 100000 events per second. Importantly, whether or not each pixel has its own particle counter, the architecture of the detector is such that it has a count rate capability of at least 1000 events per second per pixel.

The charge received at the particle counter 112b from its corresponding pixel 112a is first amplified by the amplifier and is then passed through the discriminator. The discriminator typically has adjustable lower and upper thresholds although it may contain only one threshold level or more than two threshold levels. A lower threshold acts as a high pass filter, i.e. only events with an energy greater than the threshold value will be counted; conversely an upper threshold acts as a low pass filter, i.e. only events with an energy less than the threshold value will be counted. In other words the thresholds can be set to discriminate between particles of different energies, for example electrons and X-rays. It is to be pointed out that, due to the filtering by energy rather than charge of particle type, a received X-ray and electron of the same energy will produce the same output signal.

The counter then counts any event that meets the requirement of the threshold. Thus, if the lower threshold is set at a first level in accordance with an energy E1 then only incident particles with energy of E1 or greater are recorded. Similarly, if the upper threshold is set at E2 then only received particles with energy of less than E2 will be recorded. Energy resolutions of around 2.5 keV have been demonstrated, which is sufficient for separating the low and high energy contributions to Kossel and EBSD signals or to isolate a band of energies around an X-ray line of interest for Kossel.

If the discriminator has two adjustable thresholds then an electronic band-pass filter may be effected. The upper threshold can be set to a level corresponding to an energy E2 and the lower threshold set to a level corresponding to E1<E2, thus the particle counter counts all events in the energy range [E1:E2]. The energy range [E1:E2] is preferably set to suit one particular X-ray line and obtain a Kossel pattern. The thresholds E1 and E2 can then be set to a different pair of values to suit a different X-ray line. Control of the adjustable thresholds enables the minimisation of background either side of the X-ray line. This is far more convenient than the implementation of foils in the "pseudo" Kossel method, and does not require any coating of the sample.

Even if only a single adjustable threshold is available, a band-pass filter can still be effected. For example, the energy range [E1:E2] can be detected using a discriminator with only a single adjustable lower threshold by firstly acquiring a first data set with the lower threshold corresponding to E1 and a second data set with a lower threshold corresponding to E2>E1 and subtracting the E2 data set from the E1 data set. A similar process can be carried out if the single threshold is an upper threshold.

The particle counters generate output signals only for those events of interest, in other words particles that lie within a chosen energy range set by the discriminator. Therefore background can be minimised since, although background particles (such as background X-rays in EBSD analysis) will generate an electronic signal in the pixel 112a due to electron-hole pair formation, this electronic signal will not satisfy the desired threshold requirements and will not be counted, and the signal to background ratio is thereby improved.

The output signal from each particle counter 112b is fed along coupling 113 to the image processing unit which generates image data. This is typically in the form of a diffraction pattern which is then displayed on the display unit 108. The output signal from each particle counter 112b is a binary output—either an event satisfied the energy threshold and was counted or it was not. The diffraction pattern is generated by recording the intensity of counts at each pixel location and the spatial resolution is set by the pixel size, which is typically in the region of micrometers. Noise in the diffraction patterns from background particles is reduced due to the thresholding set by the discriminators in the particle counters. Of course, there will be some "background" particles that will be counted by the detector, even with thresholding introduced. For example, in the case of using a high-pass thresholding for EBSD experiments, there will be some "background" particles, such as X-rays, that have great enough energy to satisfy the energy threshold criteria. However, the number of background particles counted as a whole will be significantly reduced due to the introduced energy thresholding. The diffraction pattern can then be further analysed as desired.

Typical beam energies used in SEM microdiffraction experiments such as EBSD and Kossel analyses are around 20 keV; however, energies in the range 2 keV to 50 keV can be used. For EBSD analysis, pattern acquisition times are typically a few milliseconds whereas seconds or minutes are typically needed for Kossel patterns.

The type of detector described in the embodiment of FIG. 3 is a "direct detector". Such a detector is capable of detecting any type of particle satisfying the energy thresholds, for example electrons, X-rays and light photons. The invention is not limited to direct detectors however, and other types of detector can be used that are capable of imaging and particle counting at a suitable rate per pixel. The direct detector could have a surface coating such as a scintillator that converts energy to light, provided the response time is short enough to allow the signal from individual particles to be resolved. One example of another direct detector type that could be used is a silicon strip detector. Detectors using sequential readout such as CCDs generally are unable to count at a fast enough rate; however in principle such detectors can be used.

In Kossel analysis the signal of interest is X-rays produced by interaction of the electron beam with the sample and which are diffracted by the lattice planes in the sample. Conventionally, as described hereinabove, in order to filter out the background signal of backscattered electrons, a filter 3 is used, as seen in FIG. 1. In the present embodiment, the filter 3 is implemented within the detector 111, more specifically in the particle counters 112b. In other words, instead of filtering the particles before reaching the detector (by using filter 3 for example), in the present embodiment every particle incident on the sensing element produces a charge pulse signal, and it is the particle counters 112b that carry out the filtering on these charge pulse signals. Therefore, in the arrangement of FIG. 2, the filter 3, the phosphor screen 4 and the optical coupling 5 of the conventional apparatus seen in FIG. 1 are not required.

An additional benefit of the electronic thresholding is to provide a band-pass energy filter to maximise the signal due to a particular energy or wavelength of X-rays so that the Kossel diffraction pattern is simplified and not a mixture of patterns produced by different element characteristic lines. This benefit is difficult to realise with a material absorption filter 3.

In EBSD analysis, the signal of interest is elastically scattered electrons from the sample with energy approximately equal to the primary energy of the electron beam. Inelastically scattered electrons do not contribute to the desired diffraction pattern signal and are thus a source of background noise, together with low energy X-rays. In the present invention these particles contributing to the background noise can be filtered out by setting the discriminator of each pixel to act as a high-pass filter such that only particles above a certain energy are counted; thus only elastically scattered electrons contributing to the desired EBSP are counted. For example, with the current technology, an effective threshold would be set at an energy 2 keV below the primary beam energy.

As a summary, by choosing suitable particle counter thresholds, it is possible to separate contributions from electrons and X-rays, thus:

1. Kossel diffraction patterns obtained from X-rays can be improved by excluding high- and low-energy electrons with a band-pass filter implemented in each particle counter 112b.
2. Kossel diffraction patterns of a compound sample (generated by particular characteristic X-rays from a single element in that compound) can be made simpler to interpret by excluding both different characteristic X-rays and high- and low-energy electrons with a band-pass filter implemented in each particle counter 112b.
3. EBSD patterns can be improved by excluding low-energy electrons and X-rays by using a high-pass filter implemented in each particle counter 112b.

Figure 4:
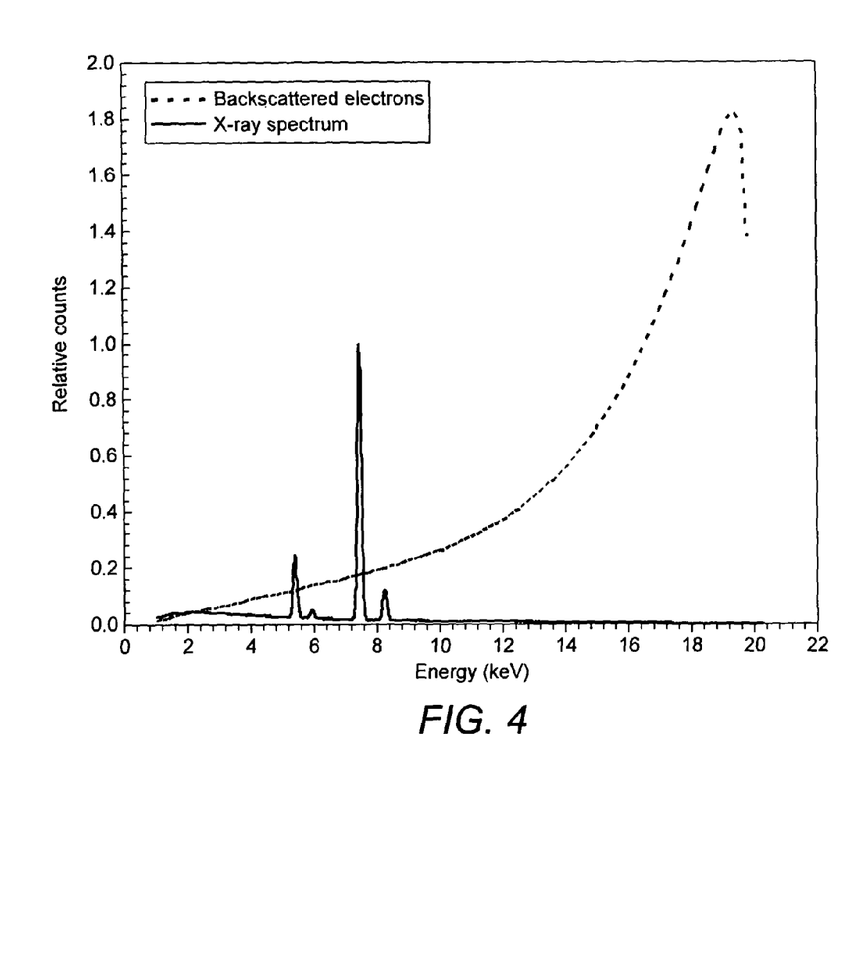
FIG. 4 is a chart showing the spectral contributions from backscattered electrons and X-rays from a Ni—Cr alloy specimen exposed to a beam of 20 keV electrons, to illustrate the use of energy thresholding at a detector according to one embodiment of the invention.

FIG. 4 shows a graph of counts against energy of spectra from a Cr—Ni alloy, excited by a 20 keV primary electron beam that reach the detector. It is useful to illustrate the use of energy thresholding in order to improve signal to background ratio in detected Kikuchi and Kossel diffraction patterns. Whereas the X-ray spectrum shows characteristic line emissions and a low bremsstrahlung background, the spectrum of electrons backscattered from the sample shows there are orders of magnitude more electrons than X-rays and electron energies are distributed continuously with the majority near the primary beam energy. The detected X-rays at approximately 5.4 keV and 7.5 keV form the basis for Kossel diffraction patterns. Using a band-pass filter ranging from 6.5 keV to 8.5 keV would ensure that the pattern is formed mainly from Ni Ka X-rays at 7.5 keV and would not include the high energy background electrons or the X-rays from Cr Ka at 5.4 keV.

If the same Cr—Ni alloy was used for EBSD analysis, a threshold set at 18 keV would pass the useful high energy electrons near the primary beam energy that form the Kikuchi diffraction pattern while excluding lower energy electrons and the X-ray line emissions from Cr and Ni that would add background noise to the pattern.

The detector 111 therefore allows for convenient and high-sensitivity analysis of the sample by different micro-diffraction techniques such as Kossel and EBSD analysis. Advantageously, the discriminators of each particle counter 112b can be utilised to provide different thresholds suitable for Kossel analysis and EBSD analysis separately. Two modes of operation, namely Kossel and EBSD, may be put into effect within the same apparatus by electronic control rather than physical intervention. In Kossel mode, an appropriate band-pass filter is set using the electronic thresholding of the discriminators, and similarly the EBSD mode is invoked by selecting an appropriate high-pass filter in the particle counters. The appropriate filters are chosen depending on the beam energy and sample used in the particular experiment. The use and manipulation of different and delicate absorption filters, bulky grid electrodes and high voltages is not required. Further, analysis by both techniques may be carried out at the same sample position in the same instrument (such as an SEM) without inconvenient manipulations.

Figure 5:
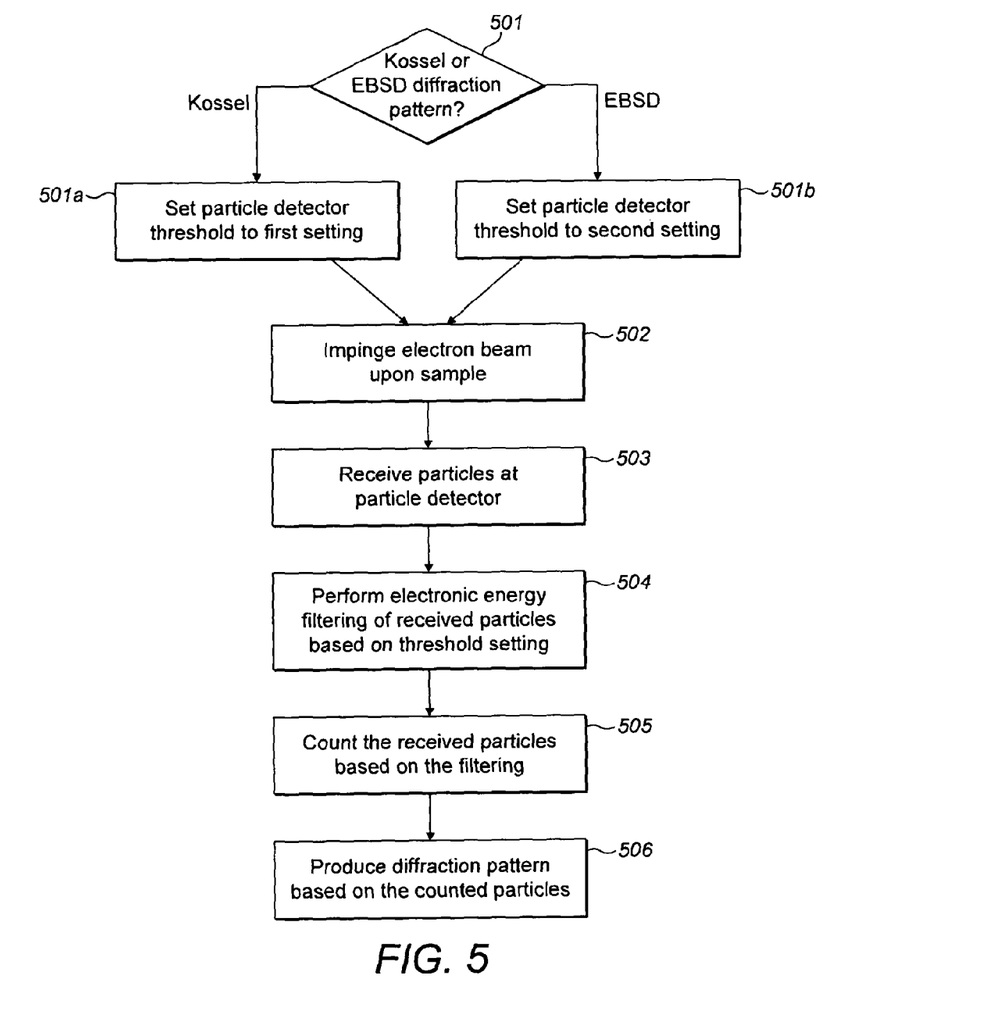
FIG. 5 is a flow chart summarising a process according to one embodiment of the present invention.

FIG. 5 is a flow diagram summarising the process according to one embodiment of the present invention. At step 501, a user of the particle detector (such as a "direct detector") decides whether a Kossel or EBSD diffraction pattern is desired at that time. If a Kossel diffraction pattern is desired, the particle detector threshold is set to a first setting (step 501a). As described above, this will typically be a band-pass filter. Alternatively, if an EBSD experiment is to be performed, the particle detector threshold is set to a second setting (step 501b). As described above, this is typically a high-pass filter.

The process then continues to step 502, where an electron beam is impinged upon the sample. This is conventionally carried out in a scanning electron microscope. Typical beam energies used in SEM microdiffraction experiments such as EBSD and Kossel analyses are around 20 keV; however, energies in the range 2 keV to 50 keV can be used.

At step 503 the particles due to interaction of the incident electron beam with the sample are received at the particle detector. As previously described, the particle detector indiscriminately receives particles, and so the received particles include both "signal" particles and background particles. The count rate capability of the particle detector is at least 1000 events per second, preferably 10000 events per second. Higher count rate capabilities are also envisaged, such as 100000 events per second.

At step 504, the particle counters of the particle detector perform electronic energy filtering of the received particles based upon the chosen threshold at step 501a/501b, and at step 505 the received particles are counted based upon the filtering. For example, if a high-pass filter has been selected for EBSD analysis, background low-energy inelastically scattered electrons and Kossel X-rays will be filtered out by the electronic filtering, and only particles with energy greater than the threshold—predominantly "signal" elastically scattered electrons—will be counted. This advantageously improves the signal to noise ratio of the analysis. Typically the filtering and counting steps are performed for each of the array of pixels of the particle detector simultaneously.

At step 506, the desired diffraction pattern (EBSD or Kossel) is produced from the counted particles in step 505. This is typically performed on an image processing unit and the output displayed on a suitable display device.

EXAMPLE

An example of a direct detector is the Medipix2 detector, which is an array of 256×256 pixels each of area 55 $\mu m^2$, which has been demonstrated to have an energy resolution of approximately 2.5 keV. The Medipix2 detector is also capable of counting up to $10^6$ Hz/pixel, which meets the requirement to deal with the electron and x-ray count rates seen in typical EBSD and Kossel experiments.

The invention claimed is:

1. Apparatus for detecting one or each of Kikuchi and Kossel diffraction patterns, the apparatus comprising:
   an electron column adapted in use to provide an electron beam directed towards a sample, the electron beam having an energy in the range 2 keV to 50 keV, and;
   a particle detector for receiving and counting particles from the sample due to interaction of the electron beam with the sample, the detector comprising an array of pixels and having a count rate capability of at least 1000 particles per second for each pixel, and wherein;
   the particle detector is adapted to provide electronic energy filtering of the received particles in order to count the received particles which are representative of the said diffraction pattern.

2. The apparatus of claim 1, wherein the detector generates an output signal in accordance with the energy of each received particle.

3. The apparatus of claim 1, wherein the received particles have a range of energies including energies representative of the said diffraction pattern and energies representative of a background.

4. The apparatus of claim 1, wherein the detector has a count rate capability, for each pixel, of at least 10000 particles per second.

5. The apparatus of claim 1, wherein the particle detector is adapted to provide electronic energy filtering with respect to at least one adjustable energy threshold.

6. The apparatus of claim 5, further comprising a control device operable, in use, to adjust the at least one adjustable energy threshold between a first setting and a second setting.

7. The apparatus of claim 6, wherein at the first setting each particle counter is adapted to provide electronic energy filtering, with respect to at least one adjustable energy threshold, acting as a band-pass filter; and at the second setting each particle counter is adapted to provide electronic energy filtering, with respect to at least one adjustable energy threshold, acting as a high-pass filter.

8. The apparatus of claim 1, wherein the electronic energy filtering is adapted to distinguish between received particles having an energy representative of the said diffraction pattern and received particles having an energy representative of a background.

9. The apparatus of claim 1, wherein the particle detector is adapted to convert the energy of each received particle directly into an electronic signal, and said electronic energy filtering acts on said electronic signals.

10. The apparatus of claim 1, wherein the detector comprises at least one particle counter.

11. The apparatus of claim 10, wherein the array of pixels and the at least one particle counter are a unitary member.

12. The apparatus of claim 10, wherein each pixel comprises a semiconductor substrate for sensing particles.

13. The apparatus of claim 10, wherein each pixel has a corresponding particle counter.

14. The apparatus of claim 13, wherein each particle counter has a count rate capability of at least 1000 particles per second.

15. The apparatus of claim 13, wherein each particle counter has a count rate capability of at least 10000 particles per second.

16. The apparatus of claim 13, wherein the detector comprises an array of particle counters corresponding to the array of pixels.

17. The apparatus of claim 10, wherein each particle counter produces an individual output signal in accordance with the energy of each received particle.

18. The apparatus of claim 10, wherein each particle counter is adapted to provide electronic energy filtering with respect to at least one adjustable energy threshold.

19. The apparatus of claim 18, wherein each particle counter is adapted to provide electronic energy filtering, with respect to at least one adjustable energy threshold, acting as a high-pass filter.

20. The apparatus of claim 18, wherein each particle counter is adapted to provide electronic energy filtering, with respect to at least one adjustable energy threshold, acting as a band-pass filter.

21. The apparatus of claim 18, wherein each particle counter is adapted to provide electronic energy filtering, with respect to at least one adjustable energy threshold, acting as a low-pass filter.

22. The apparatus of claim 1, wherein the electron column is a part of a scanning electron microscope.

23. The apparatus of claim 1, further comprising an image processing unit adapted to generate image data from the detector.

24. The apparatus of claim 1, wherein the detector is a direct detector.

25. A method for detecting one or each of Kossel and Kikuchi diffraction patterns, the method comprising:
    operating an electron column such that an electron beam having an energy in the range 2 keV to 50 keV impinges upon a sample;
    receiving, at a particle detector, particles from the sample due to interaction of the electron beam with the sample, the particle detector comprising an array of pixels and having a count rate capability of at least 1000 particles per second;
    electronically filtering, at the particle detector, the energy of each received particle; and
    counting, at the particle detector and based on the electronic filtering, the received particles representative of the said diffraction pattern.

26. The method of claim 25, wherein the steps of electronically filtering and counting are carried out for each of the array of pixels simultaneously.

27. The method of claim 25, wherein the energy threshold is adjustable and wherein the method further comprises the step of adjusting the adjustable energy threshold between a first setting and a second setting.

28. The method of claim 27, further comprising the step of adjusting the energy threshold between a plurality of settings and at each setting generating an output signal from the detector.

29. A method of detecting Kossel and Kikuchi diffraction patterns, comprising the method of claim 27, wherein when detecting a Kassel diffraction pattern the adjustable energy threshold is set to a first setting, and when detecting a Kikuchi diffraction pattern the adjustable energy threshold is set to a second setting.

30. The method of claim 29, wherein the first setting is a band-pass filter and the second setting is a high-pass filter.

* * * * *